United States Patent
Wilson et al.

(10) Patent No.: US 7,184,217 B2
(45) Date of Patent: Feb. 27, 2007

(54) OPTICAL STACK OF LAMINATED REMOVABLE LENSES FOR FACE SHIELD, WINDOWS, AND DISPLAYS

(76) Inventors: Bart Wilson, 27128 Paseo Espada Suite 1503, San Juan Capistrano, CA (US) 92675; Seth Wilson, 27128 Paseo Espada Suite 1503, San Juan Capistrano, CA (US) 92675; Stephen S. Wilson, 27128 Paseo Espada Suite 1503, San Juan Capistrano, CA (US) 92675

( * ) Notice: Subject to any disclaimer, the term of this patent is extended or adjusted under 35 U.S.C. 154(b) by 0 days.

(21) Appl. No.: 10/974,372

(22) Filed: Oct. 27, 2004

(65) Prior Publication Data

US 2005/0083582 A1   Apr. 21, 2005

Related U.S. Application Data

(63) Continuation of application No. 10/845,228, filed on May 13, 2004, now Pat. No. 6,847,492, which is a continuation of application No. 10/050,366, filed on Jan. 16, 2002, now abandoned, which is a continuation of application No. 09/449,318, filed on Nov. 24, 1999, now Pat. No. 6,388,813.

(51) Int. Cl.
*G02B 27/14* (2006.01)
*G02B 5/08* (2006.01)
*G02B 5/20* (2006.01)
*F21V 9/04* (2006.01)
*F21V 9/06* (2006.01)

(52) U.S. Cl. ...................................... 359/630; 359/359

(58) Field of Classification Search ................ 359/359, 359/630, 631; 351/44, 47; 2/424–435, 9–13, 2/15
See application file for complete search history.

(56) References Cited

U.S. PATENT DOCUMENTS

| 2,511,329 A | 6/1950 | Craig |
| 3,785,102 A | 1/1974 | Amos |
| 4,076,373 A | 2/1978 | Moretti |
| 4,090,464 A | 5/1978 | Bishopp et al. |
| 4,138,746 A | 2/1979 | Bergmann |
| 4,301,193 A | 11/1981 | Zuk |
| 4,332,861 A | 6/1982 | Franz et al. |
| 4,380,563 A | 4/1983 | Ayotte |
| 4,716,601 A | 1/1988 | McNeal |
| 4,842,919 A | 6/1989 | David et al. |
| 4,934,792 A | 6/1990 | Tovi |

(Continued)

FOREIGN PATENT DOCUMENTS

DE   3637 188 A1   10/1986

(Continued)

*Primary Examiner*—Alicia Harrington
(74) *Attorney, Agent, or Firm*—Stetina Brenda Garred & Brucker

(57) ABSTRACT

A stack of laminated transparent lenses consists of two alternating optically clear materials in intimate contact. The materials are a plastic lens and clear adhesive. The adhesive is uninterrupted. The lens and the adhesive have refraction mismatch of less than 0.2. A tab portion is part of each lens acts as an aid in peeling away the outermost lens after contamination of the lens layer during racing conditions. The lens stack can be mounted to the posts on the face shield or laminated directly to a windshield.

17 Claims, 5 Drawing Sheets

U.S. PATENT DOCUMENTS

| | | |
|---|---|---|
| 5,002,326 A | 3/1991 | Westfield et al. |
| 5,104,929 A | 4/1992 | Bilkadi |
| 5,194,293 A | 3/1993 | Foster |
| 5,420,649 A | 5/1995 | Lewis |
| 5,443,877 A | 8/1995 | Kramer et al. |
| 5,471,036 A | 11/1995 | Sperbeck |
| 5,512,116 A | 4/1996 | Campfield |
| 5,592,698 A | 1/1997 | Woods |
| 5,633,049 A | 5/1997 | Bilkadi et al. |
| 5,671,483 A | 9/1997 | Reuber |
| 5,694,650 A | 12/1997 | Hong |
| 5,972,453 A | 10/1999 | Akiwa et al. |
| 5,991,072 A | 11/1999 | Solyntjes et al. |
| 6,085,358 A | 7/2000 | Cogan |
| 6,388,813 B1 | 5/2002 | Wilson et al. |
| 6,461,709 B1 | 10/2002 | Janssen et al. |
| 6,536,045 B1 | 3/2003 | Wilson et al. |

FOREIGN PATENT DOCUMENTS

| | | |
|---|---|---|
| EP | 0671 258 A2 | 2/1995 |
| GB | 2310862 A | 3/1997 |
| JP | 6-53832 | 5/1961 |
| JP | 10-167765 | 2/1997 |

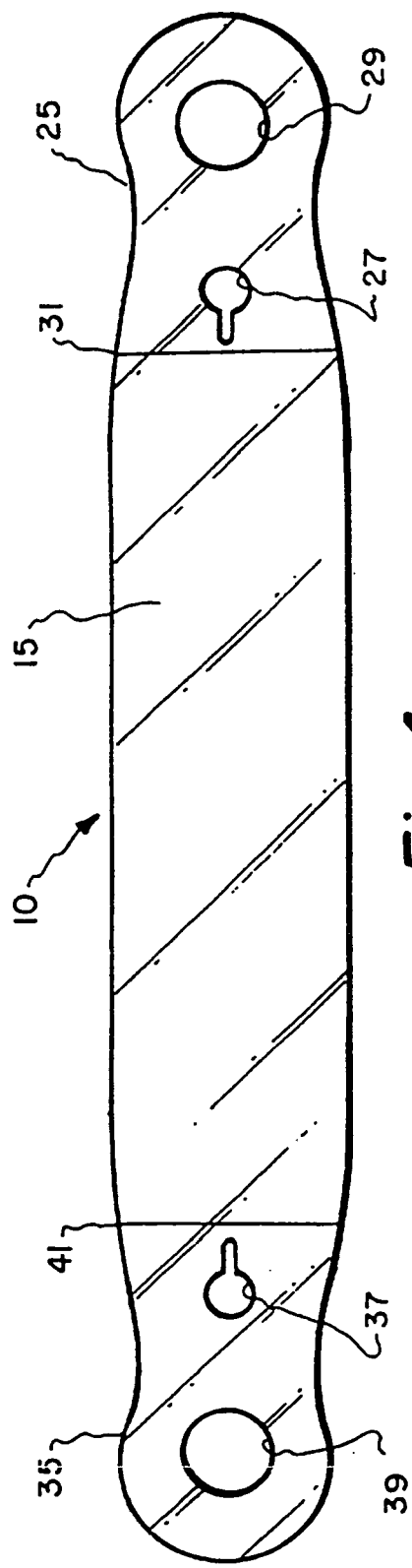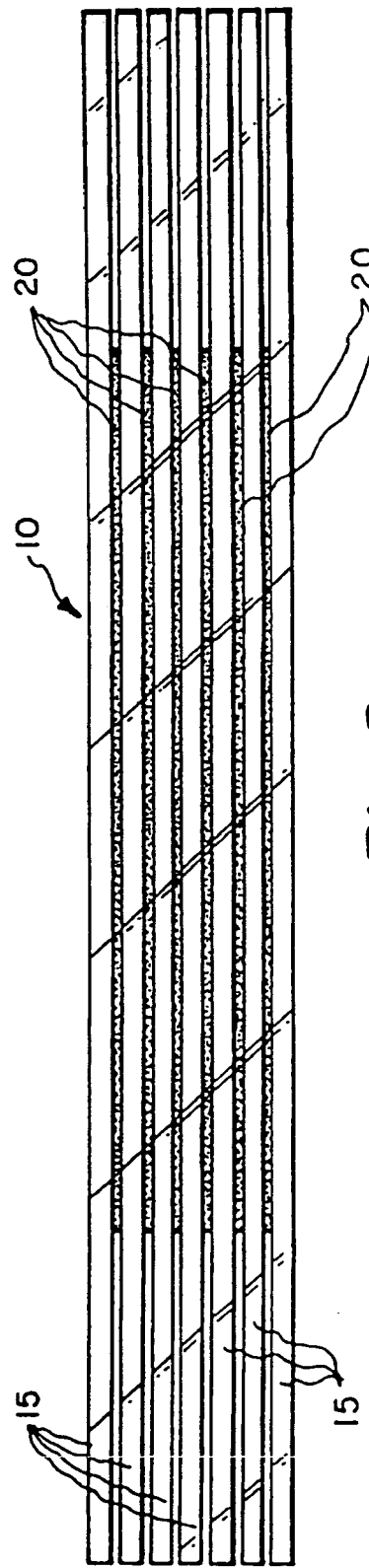

OPTICAL STACK OF LAMINATED REMOVABLE LENSES FOR FACE SHIELD, WINDOWS, AND DISPLAYS

CROSS REFERENCE TO RELATED APPLICATIONS

This application is a continuation of application Ser. No. 10/845,228, filed May 13, 2004, now U.S. Pat. No. 6,847, 492, which is a continuation of application Ser. No. 10/050, 366, filed Jan. 16, 2002 now abandoned, which is a continuation of application Ser. No. 09/449,318, filed Nov. 24, 1999, now U.S. Pat. No. 6,388,813, the entire contents of which are expressly incorporated herein by reference.

BACKGROUND OF THE INVENTION

1. Field of the Invention

The present invention pertains to the following areas of technology: Apparel—Guards and Protectors; for wearer's head and face; eye shields such as goggles having a lens-cover plate; and windshield covers.

2. Description of the Prior Art

Face shields are employed in environments where contamination of the eyes may occur. It is well known in the art that flexible transparent lenses affixed by numerous methods are overlaid on the face shield for protection. The lenses are easily removed and discarded when visibility is reduced from the accumulation of dirt or other contaminants. In motor sports for instance, multiple layers of transparent lenses are overlaid on the face shield, each being sequentially removed as they become contaminated, because they reduce the visibility of the operator. The drawback of the lenses in the prior art is that each transparent lens applied over the face shield is itself a hindrance to good visibility due to its optical index of refraction. Most common materials used as plastics have optical indexes of refraction ranging from 1.47 to 1.498. The index mismatch between the removable lens and air (air has an optical index of 1.00) causes a reflection of 4% of the light that would normally come to the operator's eyes. This reflection effect is additive for each additional surface to air interface. Then for each removable lens having two surfaces, the reflections are 8%. Thus a stack of seven lenses would reflect 42% of the light away from the operator thereby reducing the brightness of the objects viewed. A second optical phenomenon occurs simultaneously that also reduces visibility. The reflections are bi-directional and thus make the lens stack appear as a semi-permeable mirror to the operator. This mirror effect further reduces visibility, because the light that passes through the lens stack reflects off of the operator's face and then reflects off of the lens stack into the operator's eyes. The effect to the operator is that he sees his own image on the inside of the stack nearly as brightly as the objects viewed on the outside. This significantly reduces visibility.

Another drawback to this stacking arrangement is that moisture exhaled by the operator's breath can cloud or fog-up the lenses also reducing visibility. The air spaces between each lens allows the moisture to enter this area.

SUMMARY OF THE INVENTION

An object of the present invention is to provide a series of easily removable optically clear lens stacks that do not cause reflection to the operator's eyes. The prior art discloses reflective lens stacks that do cause reflections to the operator's eyes. An example of this type of prior art of reflective lens stacks is disclosed in U.S. Pat. No. 5,592,698 issued on Jan. 14, 1997 to Woods.

Refraction is the change in the direction in which waves travel when they pass from one kind of matter into another. Waves are refracted (bent) when they pass at an angle from one medium into another in which the velocity of light is different. The amount that a ray of a certain wavelength bends in passing from one medium to another is indicated by the index of refraction between the two mediums for that wavelength. The index of refraction indicates the amount that a light ray bends as it passes out of one substance and into another. When light passes from air to a denser substance, such as Mylar film, it slows down. If the light ray enters the Mylar film at any angle except a right angle, the slowing down causes the light ray to bend at the point of entry. This bending is called refraction. The ratio of the speed of light in air to its speed in the Mylar film is the Mylar film's index of refraction.

The present invention includes a series of alternating optically clear films whose indexes of refraction are matched to within 0.2 and which will nearly eliminate all reflections to the operator's eyes. The layers of film are adhesively laminated to one another and are compliant so there is no air between the layers. The film layers can be large and generally rectangular in shape with a tab extending from each of the film layers. The tabs can be staggered so that the user can remove the top most layer and then the next succeeding layer. This embodiment of the present invention can be applied to race car windshields, windows, visors or direct view displays such as ATM machines that are subject to contaminating environments. Accordingly, the present invention is an adhesively laminated multi-layered clear film adapted to be used on a racer's face shield, or on the windshield of a race car to keep the viewing area clean during the course of a race.

BRIEF DESCRIPTION OF THE DRAWINGS

FIG. 4 is a front elevational view illustrating the present invention before it is affixed to the face shield of the helmet.

FIG. 5. is a top view of the stackable lenses illustrating seven layers of lens held together by an adhesive applied between each lens with the thicknesses of the layers of each lens and applied adhesive highly exaggerated to clearly show the relationship between the lenses and the adhesive and also to show the end portions that do not have any adhesive between each lens layer for forming the removable tab portions at both ends of the present invention.

FIG. 7 is an exploded perspective view illustrating seven sheets of film layer and seven layers of clear adhesive interposed between each sheet of film layer. This embodiment is used for windshields, windows and the like.

FIG. 8 is a view of the laminated sheets illustrated in FIG. 7 having a rectangular shape with a series of six tabs for removing each top layer of the lenses successively as the uppermost exposed lens layer becomes soiled or otherwise contaminated.

DETAILED DESCRIPTION OF THE INVENTION

Figure 3:
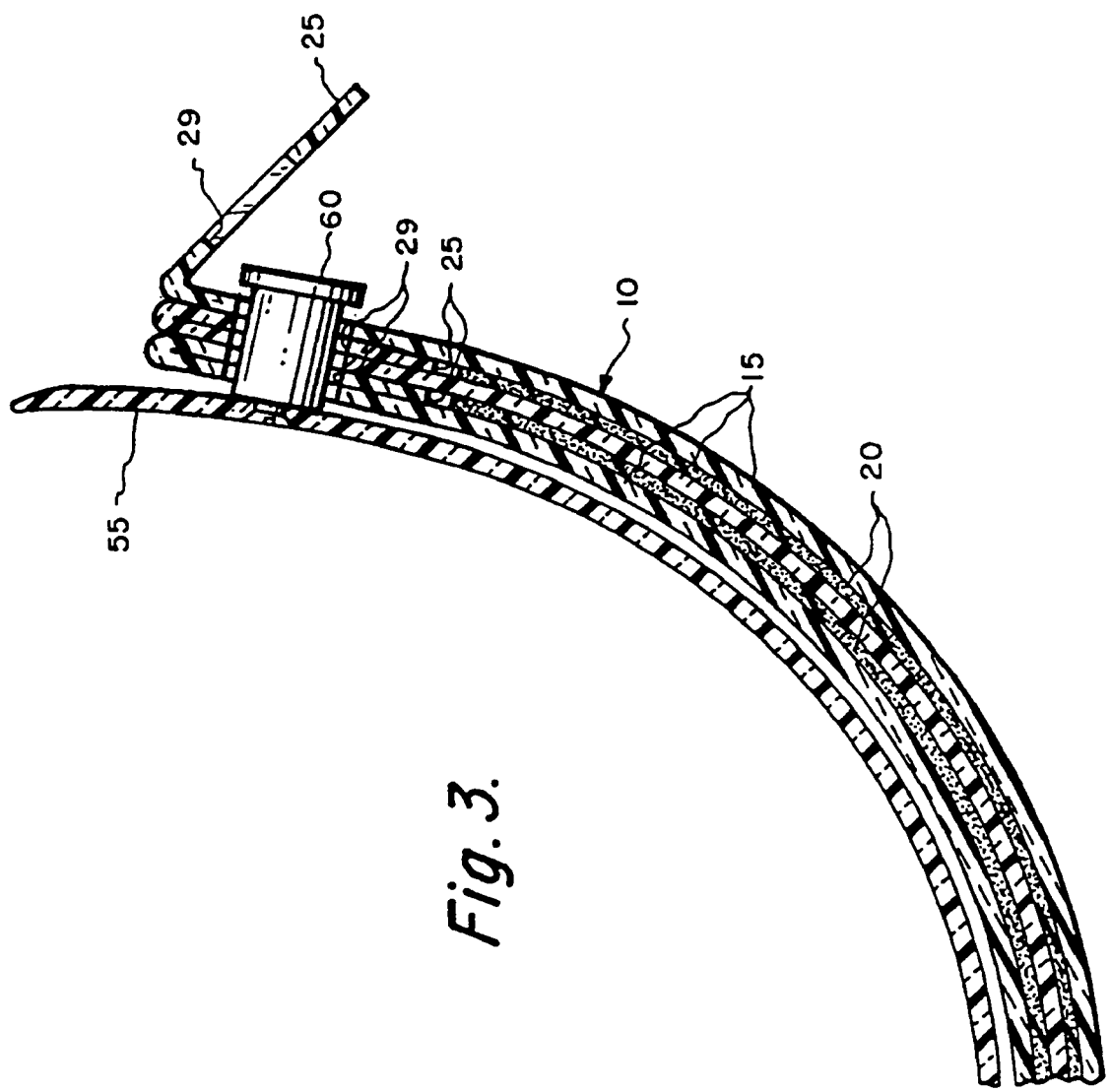
FIG. 3 is a partial sectional view taken along line 3—3 in FIG. 2. This view shows the tension post extending outwardly from the face shield with the left-side end tab portion of the present invention.

The present invention will now be discussed in detail. As stated above, FIG. 4 is a front elevational view illustrating the present invention 10 before it is affixed to the face shield of the helmet. The top view in FIG. 5 illustrates 7 layers of lenses 15 adhesively affixed to each successive lenses. The adhesive layer is numbered 20. The material used to form the lenses is preferably a clear polyester. The lens layers are fabricated from sheets of plastic film sold under the registered trademark Mylar owned by the DuPont Company. The several trademark registrations for the mark Mylar list several types of products sold under that mark, and include polyester film. The type of Mylar used in the present invention is made from the clear polymer polyethylene terephalate, commonly referred to as PET, which is the most important polyester. PET is thermoplastic—that is, it softens and melts at high temperatures. Uses of PET film include magnetic tapes and shrink wrap. The adhesive 20 used to laminate the lenses together sequentially is a clear optical low tack material. The thickness of each lens will range from 0.5 mil to 7 mil (1 mil is 0.001"). The preferred thickness will be 2 mil. Even after the adhesive material is applied to a 2 mil thickness lens, the thickness of the 2 mil thickness lenses will still be 2 mil. The adhesive has nominal thickness. As illustrated in FIG. 5, after the seven layers of film and the six layers of adhesive are laminated together, the overall thickness of the end product is 15 mils. The term "wetting" can be used to describe the relationship between the laminated film layers. When viewing through the laminated layers, it appears to be one single piece of plastic film. No reflections are evident. The end tab portions without the adhesive exhibit reflections are not a hindrance to the user, because these end portions are folded back over the posts as illustrated in FIG. 3, and do not affect the visibility of the user.

The adhesive material 20 will be a water-based acrylic optically clear adhesive or an oil based clear adhesive, with the water based adhesive being the preferred embodiment. After the seven layers are laminated or otherwise bonded together with the adhesive layers, the thickness of each adhesive layer is negligible even though the adhesive layers are illustrated in FIGS. 4 and 5 as distinct layers. FIG. 5. is a top view of the stackable lenses illustrating seven layers of lens held together by an adhesive applied between each lens with the thicknesses of the layers of lenses and applied adhesive highly exaggerated to clearly show the relationship between the lenses and the adhesive and also to show the end portions that do not have any adhesive between each lens layer for forming the removable tab portions 25 at both ends of the present invention.

Figure 6:
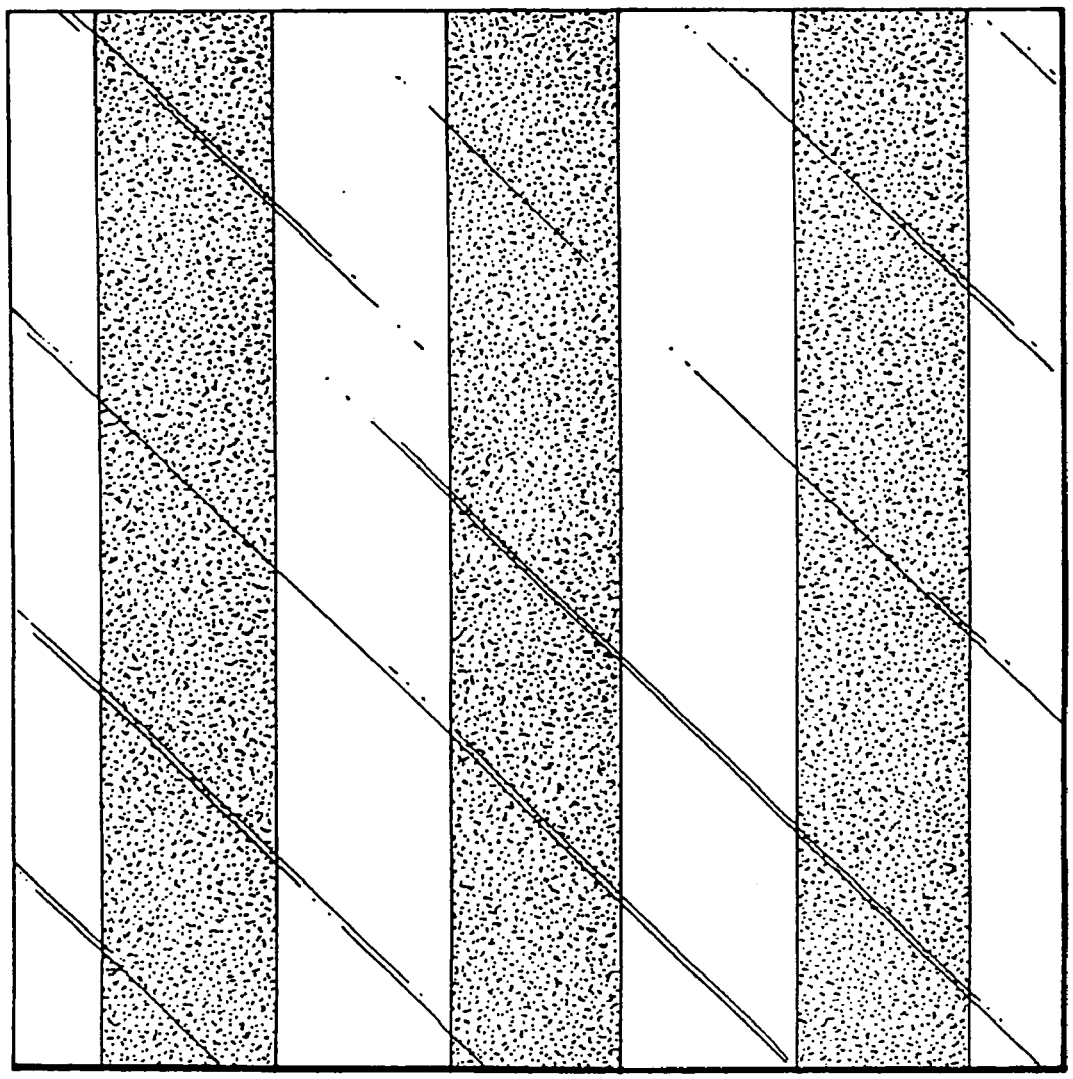
FIG. 6 illustrates a 60" wide roll of film, which will be used to cut out the optical stacks that are illustrated in FIG. 4. The gray stripes illustrate the clear adhesive, and the clear stripes illustrate the clear film without adhesive. It is to be understood that the gray stripes are for illustration purposes only, because the adhesive is clear.

The individual stackable lenses package, illustrated in FIG. 5 for use with racing helmets, can be fabricated from a roll of film as illustrated in FIG. 6. The film in FIG. 6 includes seven layers of clear polyester film, and having the water-based acrylic adhesive laminating the seven film layers to one another. Keep in mind that each layer of the lenses can be easily peeled away as the top layer exposing the next clean lens. Each succeeding lens layer can be removed as the top lens becomes contaminated with dirt and grime during racing conditions.

Figure 2:
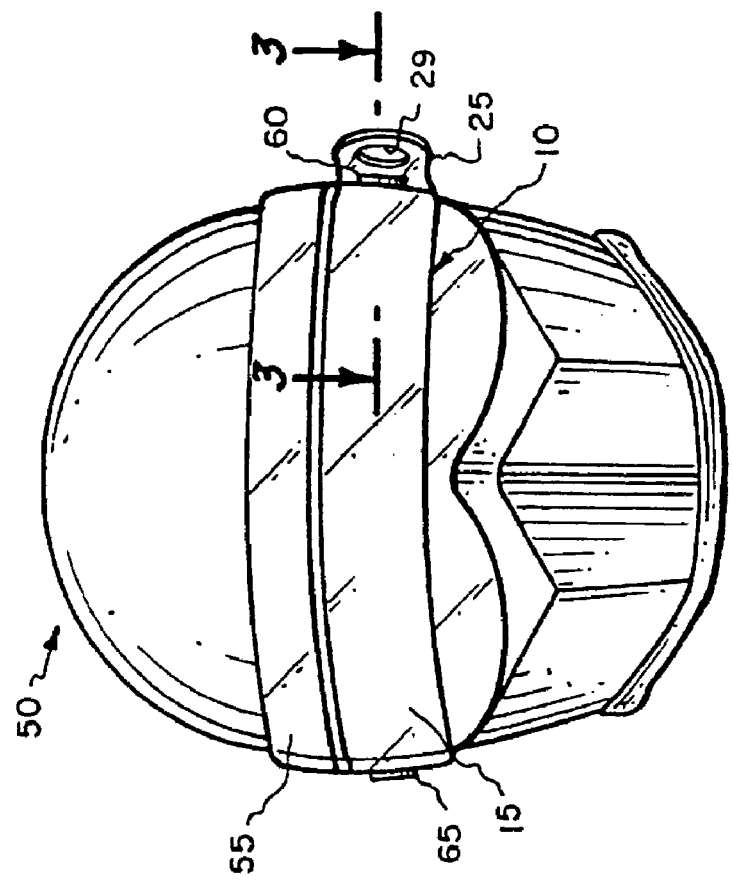
FIG. 2 is a front elevational view of the helmet shown in FIG. 1 showing the tab portion without any adhesive for allowing the wearer of the helmet to easily grasp the tab and peel-off the soiled top layer of the present invention.
Figure 1:
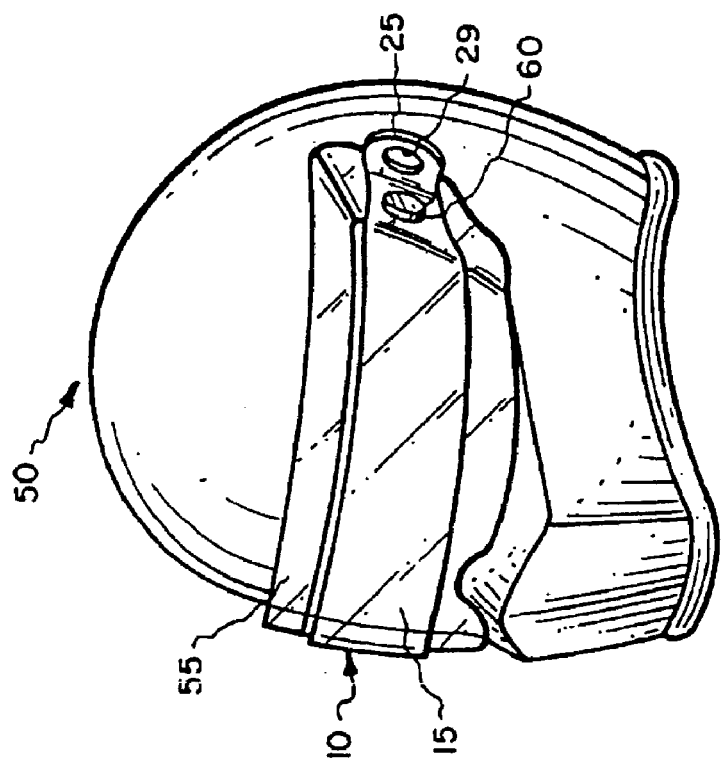
FIG. 1 is a perspective view of an off-road wearer's helmet showing one embodiment of the present invention affixed to the face shield of the helmet.

Referring back now to FIG. 3. As previously stated, FIG. 3 illustrates the tension post 60 extending outwardly from the face shield 55 with the left side end tab portion 25 of the present invention illustrated. The face shield 55 has a left tension post 60 and a right tension post 65. The present invention 10 has the following dimensions: 18" in length; 2½" in height; and about 15 mils in thickness (1 mil is 0.001"). The present invention is symmetrical about it vertical medial axis and about its horizontal medial axis. The left end has a removable tab portion 25, and the right end has a removable tab portion 35. The area 15 indicates where the adhesive 20 is applied to the layers of the lens 15. The bilateral demarcation lines 31 and 41 indicate where the adhesive stops on either side. The demarcation lines 31 and 41 also indicate where the tab portions begin. The present invention has a pair of bilateral keyhole-shaped slots 27 and 37 for demountably engaging the two helmet posts 60 and 65 respectively. The curved distance between the two helmet posts 60 and 65 is the same as the distance between the centers of the pair of slots 27 and 37. The user secures the lenses to the face shield by positioning the slots adjacent the helmet posts and passing the posts through the slots. It is preferable that the remainder of the tab portion outboard from the slot be folded back upon itself so that the finger hole is also passed through the helmet post. This is illustrated in FIG. 3. The proper installation of the present invention on the helmet requires the user to position the bottom lens of the stack through the post hole by passing the post through the slot, then folding back the remainder of the tab portion 25 so that post passes through the finger hole 29. This is done for each lens working from the bottom up until the tab portion 25 of the top lens extends unfolded as illustrated in FIG. 2. In this manner, the helmet wearer can easily put his index finger through the finger hole topmost lens layer. The clean layer below the removed layer is then exposed and the removal tab portion on the exposed layer will spring back to the unfolded position to expose the finger hole so that the helmet wearer can easily remove that layer after it becomes soiled and contaminated. The plastic material forming the lenses is resilient and will spring back to its unfolded position and extend outwardly from the face shield. The thicknesses of the layered lenses and folded tab portions illustrated in FIG. 3 are highly exaggerated to clearly show the folding relationship. In actual practice seven lenses and seven tab portions with be stacked into the space between the end of the post and the outer surface of the face shield. Remember that there is no adhesive between the tab portions. This allows the removal tab portions to fan out. They do not stick to one another.

The present invention as shown in the Drawing Figures has removal tab portions at both ends. This allows a right or left-handed person to easily remove the topmost layer. It also allows the driver to pull the tab with either hand depending on the circumstances of the race. It is to be understood that the present invention includes a laminated lenses with only a left tab portion 25, or only a right tab portion 35, or both a left and a right tab portion.

The windshield embodiment 100 illustrated in FIGS. 7 and 8 will now be discussed in detail. An optical stack of removable lenses for affixing to an optical window such as a racing car windshield is disclosed in FIG. 8. The embodiment 100 has a plurality of seven generally rectangular superposed removable lenses 105 adhesively affixed to one another. The outer perimeter is continuous. Each of the removable lens 105 is held to each successive lens with a clear uninterrupted adhesive layer 110 interposed between each of the removable lens. The perimeter has at least one generally straight edge portion 115. In the embodiment illustrated in FIG. 8, the perimeter is rectangular and has four straight edge portions, one for each side. It is to be understood that the invention could be practiced with only one generally straight edge portion. The area adjacent to the straight edge portion 115 has a banded portion 120 that does not have any adhesive affixed to any of the layers of film to assist in allowing each said film layer 105 to be peeled off successively along the straight edge portion. A plurality of staggered tabs 125 are affixed to the film layers one-at-a-time. The tabs 125 extend from the straight edge portions 120 to assist the user in removing the uppermost soiled and grimy film layer, and to successively remove each next clean layer as the top exposed layer becomes contaminated.

The adhesive layer can be foreshortened so as to expose successively a portion of the lens layers without optical wetting to create a grasping tab.

Figures 7, 8:
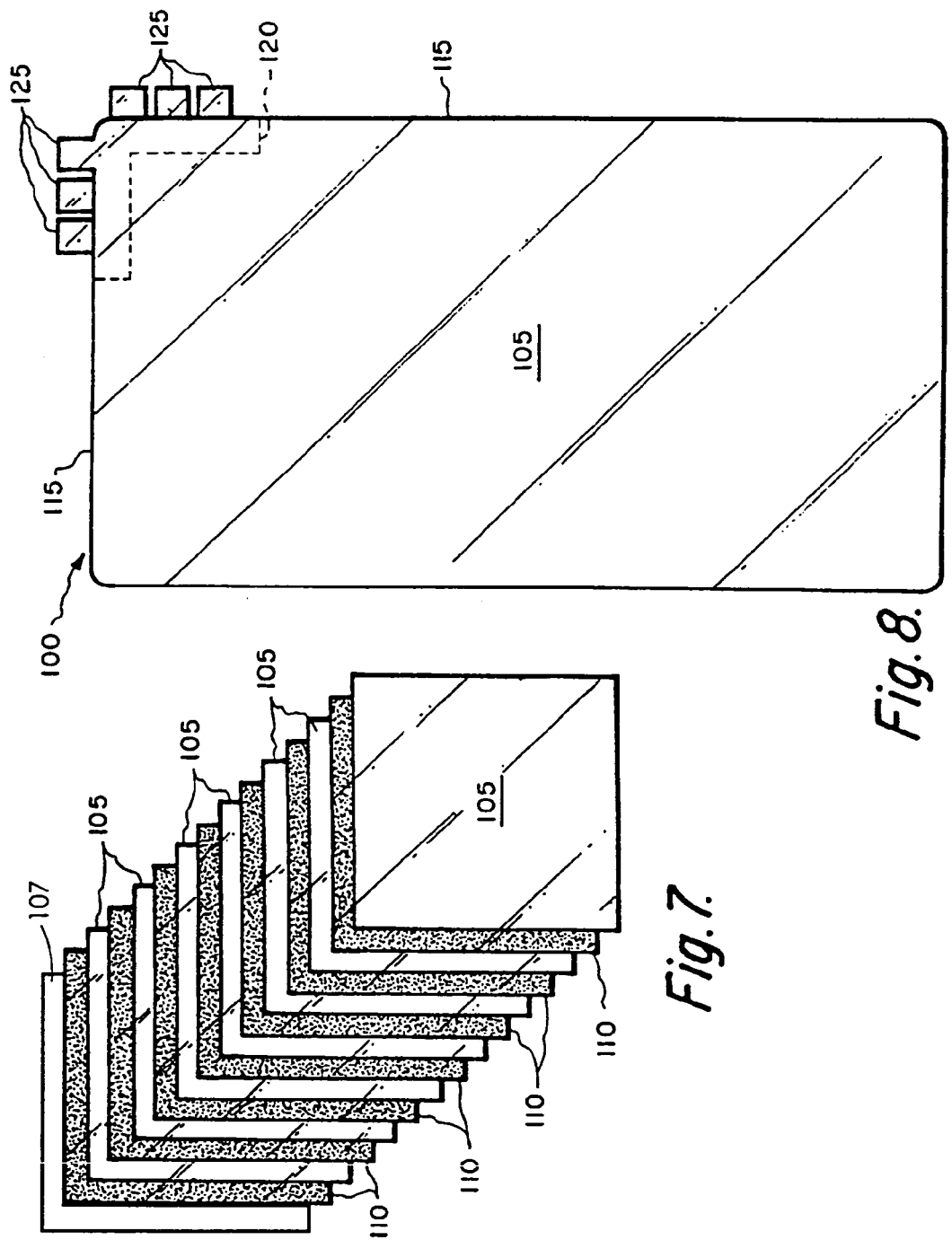

The stack of removable lenses as illustrated in FIGS. 7 and 8 can have an optically clear adhesive as the bottom last layer to aid in mounting the stack of lenses to the windshield. The stack is affixed to the windshield in much the same way that tinted window plastic film is affixed to a window. The windshield is sprayed with water and the bottom adhesive layer with the stack is then applied to the windshield. Air bubbles and the like are eliminated with a squeegee appliance. The bottom layer becomes "wetted" to the windshield.

The stack of removable lenses 100 can be applied to any type of optical window such as windshield, window, face shield, or a video display. It is common at an ATM terminal to have a video display for the customer. The surface of the display can be kept clear by using the present invention. herein in what is conceived to be the best mode contemplated, it is recognized that departures may be made therefrom within the scope of the invention which is therefore not to be limited to the details disclosed herein, but is to be afforded the full scope of the invention.

What is claimed is:

1. A stack comprising:
 a plurality of removable lenses affixed to each other and successive lenses define contact surfaces with respect to each other; and
 a clear adhesive interposed between each upper and lower lenses and adhered to the upper and lower lens contact surfaces;
 wherein a refraction mismatch between the plurality of removable lenses is less than about 0.2 such that no reflections are evident through the plurality of removable lenses.

2. The stack of claim 1, wherein a refraction mismatch between the lens and adhesive is less than about 0.2.

3. The stack of claim 2, wherein the refraction mismatch between the plurality of removable lenses is greater than the refraction mismatch between the lens and adhesive.

4. The stack of claim 2, wherein the refraction mismatch between the lens and adhesive is about 0.12.

5. The stack of claim 1, wherein the clear adhesive is a water-based adhesive.

6. The stack of claim 1, wherein the clear adhesive is an oil based adhesive.

7. The stack of claim 1, wherein a distance between the contact surfaces of each successive lenses is negligible.

8. The stack of claim 7, wherein the distance is about 1/6 mil.

9. The stack of claim 1, wherein the lens is fabricated from polymer polyethylene terephalate.

10. An optical stack of laminated removable lenses for affixing to a viewing surface consisting essentially of:
 a plurality of superposed removable lenses adhesively affixed to one another;
 each said removable lens being held to each successive lens with a clear uninterrupted adhesive layer interposed between each said removable lens such that no reflection is evident through the plurality of removable lenses;
 each said lens having a removable tab portion on at least one end which does not have any adhesive layer on either side of said tab portion such that when the optical stack of laminated removable lenses is affixed to a viewing surface a user can quickly grasp said removable tab portion for removing the top lens of the optical stack of laminated removable lenses and expose a clean lens directly underneath said removed top lens.

11. The optical stack of removable lenses as recited in claim 10 further consisting essentially of a second removable tab portion opposite the end of said removal tab portion.

12. The optical stack of removable lenses as recited in claim 10, wherein the clear uninterrupted adhesive layer has a thickness of about 1/6 mil.

13. The optical stack of removable lenses as recited in claim 10, wherein said removable lenses have indexes of refraction matched to about 0.2.

14. An optical stack of laminated removable lenses for affixing to a viewing surface consisting essentially of:
 a plurality of superposed removable lenses adhesively affixed to one another;
 each said removable lens being held to each successive lens with a clear uninterrupted adhesive layer interposed between each said removable lens and said removable lenses having indexes of refraction matched to about 0.2;
 each said lens having a removable tab portion on at least one end which does not have any adhesive layer on either side of said tab portion such that when the optical stack of laminated removable lenses is affixed to a viewing surface a user can quickly grasp said removable tab portion for removing the top lens of the optical stack of laminated removable lenses and expose a clean lens directly underneath said removed top lens.

15. The optical stack of removable lenses as recited in claim 14 further consisting essentially of a second removable tab portion opposite the end of said removal tab portion.

16. An optical stack of laminated removable lenses for affixing to a viewing surface consisting essentially of:
 a plurality of superposed removable lenses adhesively affixed to one another;
 each said removable lens being held to each successive lens with a clear uninterrupted adhesive layer interposed between each said removable lens such that no reflections are evident through the plurality of removable lenses, the layer having a thickness of about 1/6 mil;
 each said lens having a removable tab portion on at least one end which does not have any adhesive layer on either side of said tab portion such that when the optical stack of laminated removable lenses is affixed to a viewing surface a user can quickly grasp said removable tab portion for removing the top lens of the optical stack of laminated removable lenses and expose a clean lens directly underneath said removed top lens.

17. The optical stack of removable lenses as recited in claim 16 further consisting essentially of a second removable tab portion opposite the end of said removal tab portion.

* * * * *